United States Patent
Thomas et al.

(10) Patent No.: US 8,030,037 B2
(45) Date of Patent: Oct. 4, 2011

(54) PHOTOAUTOTROPHIC GROWTH OF MICROALGAE FOR OMEGA-3 FATTY ACID PRODUCTION

(75) Inventors: Swati Sebastian Thomas, Chennai (IN); Swaminathan Kumaravel, Chennai (IN)

(73) Assignee: Parry Nutraceuticals, Division of E.I.D. Parry (India) Ltd., Chennai (IN)

( * ) Notice: Subject to any disclaimer, the term of this patent is extended or adjusted under 35 U.S.C. 154(b) by 1058 days.

(21) Appl. No.: 11/651,790

(22) Filed: Jan. 10, 2007

(65) Prior Publication Data

US 2008/0166779 A1    Jul. 10, 2008

(51) Int. Cl.
| | |
|---|---|
| A01N 63/00 | (2006.01) |
| A01N 65/00 | (2009.01) |
| C11C 1/00 | (2006.01) |
| C12N 1/12 | (2006.01) |
| C12P 1/00 | (2006.01) |
| C12P 7/64 | (2006.01) |

(52) U.S. Cl. .................. 435/134; 424/93.1; 424/195.17; 435/41; 435/257.1; 435/271; 435/946

(58) Field of Classification Search .................. None
See application file for complete search history.

(56) References Cited

OTHER PUBLICATIONS

Wen, Z. and Chen, F., 2005, Prospects for eicosapentaenoic acid production using microorganisms, in Cohen, Z. and Ratledge, C. (Ed), *Single cell oils*, pp. 138-160, AOCS Press.
Kiy, T., Rüsing, M. and Fabritius, D., Production of docosahexaenoic acid by the marine microalga, *Ulkenia* sp. in Cohen, Z. and Ratledge, C. (Ed), *Single cell oils*, pp. 99-106, AOCS Press.
Molina Grima, E., García Camacho, G., Acién Fernández, F.G., 1999, Production of EPA from *Phaeodactylum tricornutum*, in Cohen, Z.,(Ed.), *Chemicals from microalgae* pp. 57-92, London: Taylor & Francis Ltd.
Sukenik, A., 1999, Production of Eicosapentanoic acid by the marine eustigmatophyte *Nannochloropsis*, in Cohen, Z.,(Ed.), *Chemicals from microalgae* pp. 41-56, London: Taylor & Francis Ltd.
Boussiba, A., Sandbank, E., Shelef, G., Cohen, Z., Vonshak, A., Ben-Amotz, A., Arad, S. and Richmond, A., 1988, Outdoor cultivation of the marine microalga *Isochrysis galabana* in open reactors. *Aquaculture* 72: 247-253.
Wynn, J., Behrens, P., Sundararajan, A., Hansen, J. and Apt, K., 2005, Production of single cell oils by dinoflagellates, in Cohen, Z. and Ratledge, C. (Ed), *Single cell oils*, pp. 86-98, AOCS Press.
Cohen, Z. and Khozin-Goldberg, I, 2005, Searching for PUFA-rich microalgae, in Cohen, Z. and Ratledge, C. (Ed), *Single cell oils*, pp. 53-72, AOCS Press.
Springer, S., Franke, H., and Pulz, O., 1994, Increase of the content of polyunsaturated fatty acids in *Porphyridium cruentum* by low-temperature stress and acetate supply.*J. Plant Physiol.* 143: 534-537.
Cohen, Z., 1994, Production potential of eicosapentaenoic acid *by Monodus subterraneus*. *J. Am. Oil Chem. Soc.* 71:941-945.
Vazhappilly, R., Chen, F., 1998, Eicosapentaenoic acid and docosahexaenoic acid production potential of microalgae and their hetertrophic growth. *J. Am. Oil Chem Soc.* 75:393-397.
Seto, A., Wang, H.L., Hesseltine, C.W., 1984, Culture conditions affect eicosapentaenoic acid content of *Chlorella minutissima*. *J. Am. Oil Chem. Soc.* 61:892-894.
Sukenik, A. 1991, Ecophysiological considerations in the optimization of eicosapentaenoic acid production by *Nannochloropsis* sp. (Eustigmatophyceae). *Bioresource Technology* 35:263-269.

*Primary Examiner* — Debbie K Ware
(74) *Attorney, Agent, or Firm* — Hugh McTavish

(57) ABSTRACT

The invention provides methods of cultivating microalgae photoautotrophically outdoors to prepare concentrated microalgae products containing eicosapentaenoic acid (EPA) and docosahexaenoic acid (DHA) docosahexaenoic acid, two long-chain polyunsaturated fatty acids found in fish oil that are very important for human and animal health. It also provides concentrated microalgae products containing EPA and DHA and purified lipid products containing EPA and DHA purified from microalgae. One embodiment provides a concentrated microalgae composition prepared by a process comprising: (a) cultivating microalgae photoautotrophically outdoors in open ponds under filtered sunlight in continuous or batch mode at a dilution rate of less than 35% per day; (b) harvesting the microalgae in exponential phase when cell number is increasing at a rate of at least 20% of maximal rate; and (c) concentrating the microalgae; wherein at least 40% by weight of lipids in the microalgae are in the form of glycodiacylglycerides, phosphodiacylglycerides, or a combination thereof and at least 5% by weight of fatty acids are DHA, EPA, or a combination thereof.

13 Claims, No Drawings

PHOTOAUTOTROPHIC GROWTH OF MICROALGAE FOR OMEGA-3 FATTY ACID PRODUCTION

This application claims priority under 35 U.S.C. § 119 to India National Patent Application, "Photoautotrophic Growth of Microalgae for Omega-3 Fatty Acid Production," filed Dec. 15, 2006, Applicant Parry Nutraceuticals, Inventors Swati Sebastian Thomas and Swaminathan Kumaravel.

BACKGROUND

Eicosapentaenoic acid (EPA) and docosahexaenoic acid (DHA) are Long Chain Poly-Unsaturated Fatty Acids (LCPUFA) and belong to the omega-3 family. These polyunsaturated fats play a very important role in the function of our bodies and have been shown to be important in maintaining brain, retina and cardiovascular health (1-9). These fatty acids also play an important role in inflammation and thus they are useful for fighting diseases linked to inflammation, which include cardiovascular disease and arthritis (10-12).

The nutritional importance of EPA and DHA began emerging in the mid 1980s. The paleolithic diet contained small and roughly equal amounts on Omega-6 and Omega-3 PUFAs (ratio of 1-2:1) (13). An imbalance of this ratio can cause many age related health problems and neurodegenerative diseases (14).

In the 1980s, the major source of these LCPUFAs in the human diet was from fish or from fish oil capsules. But fish stocks are declining throughout the world due to overfishing. In addition, fish accumulate methyl mercury, PCB's and other toxins in their fat tissue, and these thus contaminate fish oils.

Fish do not synthesize EPA and DHA; they accumulate them from eating phytoplankton or eating animals that eat phytoplankton. It is the phytoplankton and other microbes that are the primary producers of EPA and DHA. Thus, an alternative source of EPA and DHA is microorganisms, and particularly phytoplankton.

A search is on to find suitable organisms to produce EPA- and DHA-containing oils (15-19).

The main difference in fish oils and algal oils is their structure. Fish oils are storage lipids and are in the form of triacylglycerides. The algal lipids are a mixture of storage lipids and membrane lipids. The EPA and DHA present in algae is mostly in the form of glycolipids and a small percentage is in the form of phospholipids. Glycolipids are mostly part of chloroplast membranes and phospholipids are part of cell membranes. Since glycolipids and phospholipids comprise a maximum of approximately 10-15% of the dry weight of algae, EPA and DHA production in this form is not considered economically viable. It has been suggested that cost effective production of EPA and DHA from algae (or any other microbes) would require the use of microbial strains that could produce large amounts of triacyglycerides (21).

Marine algae rich in EPA or DHA are produced by hatcheries in greenhouses or indoors in large tanks or transparent cylinders. But such methods are expensive and commercially not viable.

Economical ways of raising microorganisms that accumulate EPA and DHA are lacking. Microalgae have the potential to be raised photoautotrophically—by photosynthesis without a reduced carbon source, using $CO_2$ as their carbon source. Since sunlight is free and land is inexpensive in some areas, it would be advantageous to raise microalgae outdoors photoautotrophically with sunlight in a way that results in accumulation of EPA and/or DHA. But culturing microalgae outdoors photoautotrophically is challenging because the cultures grow slowly and are prone to become contaminated when cultured outdoors. In addition, strains that may accumulate significant quantities of EPA or DHA under carefully controlled conditions may not accumulate as much under outdoor photoautotrophic conditions.

New sources of EPA and DHA for human nutritional supplements and as animal feed and aquaculture feed are needed. New improved methods of culturing microalgae to serve as a source of EPA or DHA are needed. Identification of microorganisms that are suitable sources of DHA and EPA for humans, seafood, and livestock is needed.

SUMMARY

The invention involves the discovery of successful methods of culturing microalgae photoautotrophically outdoors to accumulate EPA and/or DHA and thus serve as a source of EPA or DHA supplementation in human nutritional supplements or in animal feed or aquaculture feed. One embodiment of the invention involves the discovery that using a net over the cultures to filter sunlight to a reduced intensity is a key to successful cultivation of EPA-accumulating and DHA-accumulating microalgal strains. The invention also involves diluting the photoautotrophic cultures at a rate of about 15% to 30% per day. This is significantly less than the maximal doubling rate of the cultures, but allows stable maintenance of the cultures in outdoor photoautotrophic conditions and good accumulation of EPA and DHA. The invention also involves harvesting cultures in the exponential phase of cell growth, instead of stationary phase, and harvesting cultures with EPA and DHA predominantly in the form of membrane lipids instead of storage lipids. Cells in stationary phase accumulate more lipid in triacylglycerides as storage lipids. During exponential growth the cells have less storage lipid and most lipid is in membranes in the form of phospho- and glyco-diacylglycerides. The inventors have found that the photoautotrophic cultures accumulate large amounts of EPA and DHA as phospho- and glyco-diacylglycerides when harvested in exponential growth.

The invention also provides for the successful cultivation of microalgae photoautotrophically for EPA and DHA accumulation at the relatively high temperatures of above 20° C. or 30° C. This is important because others have reported better EPA and DHA accumulation at low temperatures, but microalgae grow faster at high temperatures (15, 22). Furthermore, microalgae can best be cultured outdoors year round in the tropics, but this requires culturing them at high temperatures unless expensive refrigeration systems are used.

One embodiment of the invention provides a method of preparing a concentrated microalgae composition involving: (a) cultivating microalgae photoautotrophically outdoors in open ponds under filtered sunlight in continuous or batch mode at a dilution rate of less than 35% per day; (b) harvesting the microalgae in exponential phase when cell number is increasing at a rate of at least 20% of maximal rate; and (c) concentrating the microalgae; wherein at least 40% of lipids in the microalgae are in the form of glycodiacylglycerides, phosphodiacylglycerides, or a combination thereof and at least 5% (preferably at least 10%) by weight of fatty acids are DHA, EPA, or a combination thereof.

Another embodiment provides a concentrated microalgae composition prepared by a process involving: (a) cultivating microalgae photoautotrophically outdoors in open ponds under filtered sunlight in continuous or batch mode at a dilution rate of less than 35% per day; (b) harvesting the microalgae in exponential phase when cell number is increasing at a rate of at least 20% of maximal rate; and (c) concentrating the microalgae; wherein at least 40% by weight of lipids in the microalgae are in the form of glycodiacylglycerides, phosphodiacylglycerides, or a combination thereof and at least 5% (preferably at least 10%) by weight of fatty acids are DHA, EPA, or a combination thereof.

Another embodiment provides a concentrated microalgae composition prepared by a process comprising: (a) cultivating microalgae photoautotrophically outdoors in open ponds under filtered sunlight; and (b) concentrating the microalgae; wherein at least 20% by weight of the fatty acids in the microalgae are eicosapentaenoic acid (EPA).

Another embodiment provides a concentrated microalgae composition prepared by a process comprising: (a) cultivating microalgae photoautotrophically outdoors in open ponds; and
(b) concentrating the microalgae; wherein the microalgae are cultivated at above 20° C. and the microalgae are Chlorophyta and the eicosapentaenoic acid (EPA) yield in the microalgae is at least 10 mg/liter culture.

Another embodiment provides a concentrated microalgae composition prepared by a process comprising: (a) cultivating microalgae photoautotrophically outdoors in open ponds; and
(b) concentrating the microalgae; wherein the microalgae are *Thalassiosira* sp. or *Chaetoceros* sp., and at least 20% by weight of the fatty acids in the microalgae are eicosapentaenoic acid (EPA). Preferably the EPA yield is at least 10 mg/liter culture.

Another embodiment of the invention provides a concentrated microalgae composition prepared by a process comprising: (a) cultivating microalgae photoautotrophically outdoors in open ponds under filtered sunlight; and (b) concentrating the microalgae; wherein the microalgae are Prymnesiophyta and the DHA yield is at least 3 mg/liter culture, and DHA is at least 10% by weight of total fatty acids.

Another embodiment of the invention provides a food grade dietary supplement for human consumption comprising a concentrated microalgae composition of the invention.

Another embodiment of the invention provides an aquaculture or animal feed comprising a concentrated microalgae composition of the invention.

Another embodiment of the invention provides a purified lipid composition prepared by a process involving purifying lipids from a concentrated microalgae composition of the invention, wherein the purified lipids comprise at least 5% (preferably at least 10%) by weight EPA or DHA or a combination thereof.

DETAILED DESCRIPTION

Definitions:

The term "microalgae" as used herein refers to photosynthetic organisms that are native to aquatic or marine habitats and are too small to be seen easily as individual organisms with the naked eye.

The term "photoautotrophic" as used herein refers to growth with light as the primary source of energy and carbon dioxide as the primary source of carbon.

As used herein, the term "a dilution rate of [e.g.] 30% per day" means that 30 ml of medium is added to 100 ml of culture each day, either continuously over the course of a day or in a single batch addition each day. The term "a dilution rate of less than X % per day" means that the average dilution rate over a period of days is less than X % per day and that no individual dilution during culturing is greater than X % in a single day.

As used herein, the term "maximal rate" of cell number increase refers to the maximal rate achieved at any stage during the outdoor photoautotrophic growth of the particular harvested culture being referenced.

As used herein, cultivating microalgae "outdoors in open ponds" means cultivating them exposed to unfiltered outdoor air. The ponds may be covered with a fabric cover that shades the pond or filters sunlight provided the pond is exposed to unfiltered outdoor air.

Description

The invention provides various methods for culturing microalgae photoautotrophically outdoors to produce EPA and DHA. One method used is filtering sunlight to reduce the light intensity on the photoautotrophic culture. Shade cloth or netting can be used for this purpose. We have found for most strains that the optimal solar intensity for growth, maintaining a pure culture, and omega-3 fatty acid accumulation is about 40,000 to 50,000 lux, approximately half of the 110,000 lux of full sunlight. Shade cloth or netting is suitable for filtering the sunlight to the desired intensity.

Another method used to successfully culture microalgae photoautotrophically outdoors to produce EPA and DHA is to use small dilutions and a slow dilution rate of less than 40% per day, preferably less than 35% per day, more preferably from about 15% to about 30% per day. In other embodiments, the dilution rate is 15-40% per day or 15-35% per day. In other embodiments, the dilution rate is 10-30%, 10-35%, or 10-40% per day. These smaller dilutions and lower dilution rates than are typically used help prevent contamination in outdoor photoautotrophic cultures. It also promotes thick culture growth that gives good DHA or EPA yield.

Another method used to successfully culture microalgae photoautotrophically outdoors to produce EPA and DHA is to harvest the microalgae in exponential phase rather than stationary phase. Harvesting in exponential phase reduces the risk of contamination in outdoor photoautotrophic cultures and has surprisingly been found to give good yield of EPA and DHA. Typically, to drive fat accumulation in microbial cultures, the cultures are harvested in stationary phase, since cells in stationary phase tend to accumulate storage lipids. But the inventors have found that EPA and DHA accumulate to large amounts as membrane lipids in cultures harvested in the exponential phase. The membrane lipids containing EPA and DHA are predominantly phosphodiacylglycerides and glycodiacylglycerides, rather than the triaclyglycerides found in storage lipids. The cultures are typically harvested when cell number is increasing at a rate at least 20% of the maximal rate, i.e., the maximal rate achieved at any stage during the outdoor photoautotrophic growth of the harvested culture. In specific embodiments, the cultures are harvested in exponential phase when cell number is increasing at a rate of at least 30%, at least 40%, or at least 50% of maximal rate.

With these techniques and the strains grown, the inventors have also achieved good DHA and EPA yields with culture outdoors at high temperatures. Others have reported that DHA and EPA accumulate better at low temperatures, and that a cold shock step, where a culture is grown at higher temperatures but then shifted to low temperatures, e.g., 12° C., for several days before harvest, is needed to accumulate omega-3 fatty acids (15, 22). The inventors have found that DHA and EPA accumulate to good levels in the strains used even with growth at 30-35° C. in the Indian summer. Thus, some embodiments of the invention involve outdoor photoautotrophic growth at least 20° C., at least 25° C., or at least 30° C. As used herein, reference to growth at least a given temperature means that the culture is maintained at least that temperature for a majority of the outdoor photoautotrophic culture time and a majority of the last 72 hours, 48 hours, and 24 hours before the culture is harvested.

Preferably the cultures are maintained outdoors photoautotrophically for at least 14 days.

In preferred embodiments of the methods and compositions of the invention, the microalgae are not genetically modified by recombinant DNA techniques.

In some embodiments of the methods and compositions of the invention, the microalgae are diatoms. In some embodiments the diatoms are *Thalassiosira* sp. or *Chaetoceros* sp.

In some embodiments, particularly with diatoms, or with *Thalassiosira* sp. or *Chaetoceros* sp., at least 20% by weight of the fatty acids in the microalgae are EPA.

In other embodiments, the microalgae are Chlorophyta (green algae). In some embodiments, the Chlorophyta are *Tetraselmis* sp.

In some embodiments, particularly where the microalgae are Chlorophyta, the EPA yield in the microalgae is at least 10 mg/liter culture.

Microalgae suitable for DHA production include Prymnesiophyta, more specifically those of class Prymnesiophyceae, more specifically those of order Isochrysales, more specifically *Isochrysis* sp. or *Pavlova* sp.

In some embodiments of the invention, the DHA yield is at least 3 mg/liter culture and DHA is at least 10% by weight of fatty acids in the microalgae. In other embodiments, the DH yield is at least 5 mg/liter culture and DHA is at least 10% by weight of fatty acids in the microalgae.

In particular embodiments, $CO_2$ is added to the open ponds during cultivation. This helps to neutralize pH and to enhance photoautotrophic growth.

In the methods of the invention, the EPA and DHA are typically predominantly membrane lipids and phosphodiacylglycerides or glycodiacylglycerides. In some embodiments, at least 40% of the EPA or DHA are in the form of phosphodiacylglycerides or glycodiacylglycerides or a combination thereof. In some embodiments, at least 30%, at least 50%, or at least 60% of the EPA or DHA in the microalgae are in the form of phosphodiacylglycerides or glycodiacylglycerides or a combination thereof.

The invention also provides a purified lipid composition prepared by a process comprising: purifying lipids from any of the concentrated microalgae compositions of the invention, wherein the purified lipids comprise at least 5% by weight EPA or DHA or a combination thereof. In particular embodiments, at least 20% by weight of fatty acids in the lipid composition are EPA. In other embodiments, at least 10% by weight of the fatty acids in the lipid composition are DHA.

In some embodiments of the purified lipid compositions, at least 30%, at least 40%, at least 50%, or at least 60% of the EPA or DHA or both in the composition are in phosphodiacylglycerides or glycodiacylglycerides or a combination thereof.

The invention also provides a food grade dietary supplement for human consumption containing a concentrated microalgae composition of the invention or a purified lipid composition of the invention.

Another embodiment of the invention provides an aquaculture feed or animal feed containing a concentrated microalgae composition of the invention or a purified lipid composition of the invention.

The invention will now be illustrated by the following examples. The examples are intended to illustrate the invention but not limit its scope.

EXAMPLES

Example 1

Strain:—*Thalassiosira* sp. *Thalassiosira* sp. is a diatom, and the strain used was isolated from Bay of Bengal. This strain dominates during summer months, and it was isolated from seawater collected near Chemai, India. This culture was maintained in open tubs. The strain was identified as *Thalassiosira weissflogii*. This strain was capable of growth at high temperatures (35-38° C.). The fatty acid profile was good even when the alga was grown at high temperature—with 25-30% EPA (as percentage of fatty acids).

Culturing

The lab cultures were maintained in tubs in artificial seawater medium, under fluorescent lights (3000-4000 lux) and the temperature was maintained at 25° C.

Initial expansion of the culture was done under laboratory condition in tubs. The dilution rate was 15% to 30% of the total culture volume per day. Once the volume was 40-50 liters, it was transferred to an outdoor pond. The outdoor ponds were covered with netting to control the light (40000 to 50000 lux). The dilution continued until the culture reached 100,000 liters volume. The culture was held in 500 sq. m ponds at this time, with a culture depth of 20 cm. The culture was stirred with a paddle wheel and $CO_2$ was mixed to keep the culture pH neutral. When the EPA levels in the pond reached a desirable level (10-15 mg/lit), the whole pond was harvested by filtration. The filtered biomass was washed with saltwater (15 parts per thousand concentration) and then spray dried. The mode of culturing was batch mode. The EPA productivity was 2-3 mg/lit/day.

The ponds can also be run continuously for several weeks by harvesting part of the culture, recycling the filtrate into the ponds and replenishing required nutrients.

Example 2

Strain: *Tetraselmis* sp. *Tetraselmis* sp. is in the division Chlorophyta and the class Prosinophyceae or Micromanadophyceae. This strain was obtained from the Central Marine Fisheries Research Institute, India. It was isolated from the local marine habitats in India. The culture was maintained in flasks in artificial seawater medium, and expanded as described for *Thalassiosira*. With culture outdoors in open ponds as described for *Thalassiosira*, the strain gave a good lipid yield (200-300 mg/liter) and an EPA content of 6-7% of fatty acids.

Example 3

Strain: *Chaetoceros* sp. This is another diatom strain obtained from the Central Marine Fisheries Research Institute, India, and isolated from local marine habitats in India. *Chaetoceros* sp. was maintained in flasks and cultivated in outdoor ponds photoautotrophically as described in Example 1. It gave similar EPA productivity and EPA content as *Thalassiosira*, described in Example 1.

Example 4

Strain: *Isochrysis* sp. *Isochrysis* is in the Prymnesiophyta, class Prymnesiophyceae, order Isochrysidales. It was obtained from the Central Marine Fisheries Research Institute, India, and isolated from local marine habitats in India. It was maintained and grown as described in Example 1. It was expanded from laboratory culture to a 50,000 liter outdoor pond culture in 14-15 days with a dilution rate of 15-30% per day. The lipid content at harvest was 100-150 mg lipids/liter. The rate of lipid production was 25-50 mg/liter/day. DHA was 10-12% of total fatty acids.

Example 5

Harvesting and Drying:

The harvesting may be done by flocculation. The commonly used flocculants include Alum with polymer; $FeCl_3$ with or without polymer and chitosan. The concentration of flocculent will depend on the cell number in the culture before harvest. The range may vary from 100 ppm to 500 ppm. Alternatively harvesting is done by filtration using appropriate meshes. Removal of adhered chemicals (other than salt) is effected by washing the cells in low salinity water.

The harvested slurry is then taken for spray drying. If required the slurry is sometimes encapsulated to prevent oxidation. The concentration of encapsulating agent may vary from 0.1 to 1.0% on dry weight basis. Modified starch is a suitable encapsulating agent. The spray dryer used is of atomizer or nozzle type. The inlet temperature ranges from 160 to 190° C. and the outlet temperature ranges from 60 to 90° C. The spray dried powder is used immediately for extraction. If storage is needed, the powder is packed in aluminum laminated pouches and sealed after displacing the air by nitrogen. The packed powder is stored at ambient temperature until further use.

Example 6

Extraction:

Extraction of EPA/DHA is carried out using wet slurry or dry powder. Extraction is carried out using solvents. The solvents include hexane, ethanol, methanol, acetone, ethyl acetate, isopropanol and cyclohexane and water. The above solvents are used alone or a combination of two solvents. The solvent to biomass ratio depends on the starting material. If it is a slurry the ratio is 1:2 to 1:10. In the case of a spray dried powder, the ratio is 1:4 to 1:30. The extraction is carried out in an extraction vessel under inert atmosphere. Extraction temperature ranges from 25 to 60° C. and the time varies from one hour to 10 hours. Solvent addition is made one time or in parts based on the lipid level in the cells. After extraction of crude lipid, the mixture is passed through a centrifuge or filtration system to remove the cell debris. The lipid in the filtrate is then concentrated by removing the solvent by distillation. The distillation process is carried out under vacuum. The resulting product is a crude lipid extract, which contains approximately 10% omega 3 fatty acid (EPA/DHA). This lipid extract can be used as such or purified further to enrich the omega 3 fatty acids. Further purification may involve removal of unsaponifiables such as pigments, sterols and their esters.

REFERENCES CITED

1. Mostofsky, D. I., Rabinovitz, S. and Yehuda, S. 2004. The use of fatty acid supplementation for seizure management. *Neurobiol. Lipids Vol.* 3, 4 Published online Oct. 20, 2004, Available at: http://neurobiologyoflipids.org/content/3/4/.
2. Lim, G. P, Calon, F., Morihara, T., Yang, F., Teter, B., Ubeda, O., Salem, N. Jr, Frautschy, S. A. and Cole, G. M. 2005. A diet enriched with the omega-3 fatty acid docosahexaenoic acid reduces amyloid burden in an aged Alzheimer mouse model. *J Neurosci* 25: 3032-3040
3. Hoffman, D. R., Birch, E. E., Birch, D. G. and Uauy, R. D. 1993. Effects of supplementation with omega-3 long-chain polyunsaturated fatty acids on retinal and cortical development in premature infants. *Am J Clin Nutr* 57 (Suppl): 807S-812S.
4. Hoffman, D. R., Theuer, R. C., Castañeda, Y. S., Wheaton, D. H., Bosworth, R. G., O'Connor, A. R., Morale, S. E., Wiedemann, L. E. and Birch, E. E. 2004. Maturation of Visual Acuity Is Accelerated in Breast-Fed Term Infants Fed Baby Food Containing DHA-Enriched Egg Yolk. *J Nutr* 134: 2307-2313.
5. Mukherjee, P. K., Marcheselli, V. L., Serhan, C. N. and Bazan, N. G. 2004. Neuroprotectin D1: A docosahexaenoic acid-derived docosatriene protects human retinal pigment epithelial cells from oxidative stress. *PNAS* 101: 8491-8496.
6. Vanschoonbeek, K., de Maat, M. P. M., and Heemskerk, J. W. M. 2003. Fish oil consumption and reduction of arterial disease. *J Nutr* 133: 657-660.
7. Leaf, A., Xang, J. X., 1996. Prevention of cardiac sudden death by N-3 fatty acids: a review of the evidence. *J Intern Med* 240: 5-12.
8. Nestel, P., Shige, H., Pomeroy, S., Cehun, M., Abbey, M. and Raederstorff, D. 2002. The n-3 fatty acids eicosapentaenoic acid and docosahexaenoic acid increase systemic arterial compliance in humans. *Am J Clin Nutr* 76: 326-330.
9. Vanschoonbeek, K., Feijge, M. A. H., Paquay, M., Rosing, J., Saris, W., Kluft, C., L. A. Giesen, P. de Maat, M. P. M and Heemskerk, J. W. M. 2004. Variable hypocoagulant effect of fish oil intake in humans: Modulation of fibrinogen level and thrombin generation. *Arterioscler Thromb Vasc Biol* 24: 1734-1740.
10. Lopez-Garcia, E., Schulze, M. B., Manson, J. E., Meigs, J. B., Albert, C. M., Rifai, M., Willett, W. C. and Hu, F. B. 2004. Consumption of (n-3) fatty acids is related to plasma biomarkers of inflammation and endothelial activation in women. *J Nutr* 134: 1806-1811.
11. Mishra, A., Chaudhary, A. and Sethi, S. 2004. Oxidized omega-3 fatty acids inhibit NF-κB activation via a PPARα-dependent pathway. *Arterioscler Thromb Vasc Biol* 24: 1621-1627.
12. Mirnikjoo, B., Brown, S. E., Kim, H. F. S., Marangell, L. B., Sweatt, J. D. and. Weeber, E. J. 2001. Protein kinase inhibition by ω3 fatty acids. *J Biol Chem* 276: 10888-10896.
13. Simopoulos, A. P. 2002. Omega-3 Fatty acids in inflammation and autoimmune diseases. *J Am Coll Nutr* 21 (6): 495-505.
14. Song, C. and Horrobin, D. 2004. Omega-3 fatty acid ethyl-eicosapentaenoate, but not soyabean oil, attenuates memory impairment induced by central IL-1B administration. *J Lipid Res* 45: 1112-1121.
15. Wen, Z. and Chen, F., 2005, Prospects for eicosapentaenoic acid production using microorganisms, in Cohen, Z. and Ratledge, C. (Ed), *Single cell oils*, pp138-160, AOCS Press.
16. Kiy, T., Rüsing, M. and Fabritius, D., Production of docosahexaenoic acid by the marine microalga, *Ulkenia* sp. in Cohen, Z. and Ratledge, C. (Ed), *Single cell oils*, pp99-106, AOCS Press.
17. Molina Grima, E., Garcia Camacho, G., Acien Fernandez, F. G., 1999, Production of EPA from *Phaeodactylum tricornutum*, in Cohen, Z., (Ed.), *Chemicals from microalgae* pp57-92, London: Taylor & Francis Ltd.

18. Sukenik, A., 1999, Production of Eicosapentanoic acid by the marine eustigmatophyte *Nannochloropsis*, in Cohen, Z., (Ed.), *Chemicals from microalgae* pp42-56, London: Taylor & Francis Ltd.
19. Boussiba, A., Sandbank, E., Shelef, G., Cohen, Z., Vonshak, A., Ben-Amotz, A., Arad, S. and Richmond, A., 1988, Outdoor cultivation of the marine microalga *Isochrysis galabana* in open reactors. *Aquaculture* 72: 247-253
20. Wynn, J., Behrens, P., Sundararajan, A., Hansen, J. and Apt, K., 2005, Production of single cell oils by dinoflagellates, in Cohen, Z. and Ratledge, C. (Ed), *Single cell oils*, pp86-98, AOCS Press.
21. Cohen, Z. and Khozin-Goldberg, I, 2005, Searching for PUFA-rich microalgae, in Cohen, Z. and Ratledge, C. (Ed), *Single cell oils, pp.* 53-72, AOCS Press.
22. Springer, S., Franke, H., and Pulz, O., 1994, Increase of the content of polyunsaturated fatty acids in *Porphyridium cruentum* by low-temperature stress and acetate supply. *J. Plant Physiol.* 143: 534-537.

What is claimed is:

1. A method of preparing a concentrated microalgae composition comprising:
cultivating microalgae photoautotrophically outdoors in open ponds under filtered sunlight in continuous or batch mode at a dilution rate of less than 35% per day;
harvesting the microalgae in exponential phase when cell number is increasing at a rate of at least 20% of maximal rate of growth; and
concentrating the microalgae to obtain a concentrated microalgae composition having at least 40% of lipids in the microalgae in the form of glycodiacylglycerides, phosphodiacylglycerides, or a combination thereof and at least 5% by weight of fatty acids are docosahexaenoic acid (DHA), eicosapentaenoic acid (EPA), or a combination thereof;
wherein (a) the microalgae are *Tetraselmis* sp. and EPA yield in the microalgae is at least 10 mg/liter culture, (b) the microalgae are *Isochrvsis* sp. or *Pavlova* sp., (c) the microalgae are *Thalassiosira* sp. or *Chaetecoros* sp. and EPA yield in the microalgae is at least 10 mg/liter culture, or (d) the microalgae are *Tetraselmis* sp. and are cultivated at above 20° C. and EPA yield in the microalgae is at least 10 mg/liter culture.

2. The method of claim 1 wherein the microalgae are diatoms and are cultivated photoautotrophically outdoors in open ponds for at least 14 days under filtered sunlight; and at least 20% by weight of the fatty acids are EPA.

3. The method of claim 1 wherein the microalgae are cultivated at above 20° C.

4. The method of claim 3 wherein the microalgae are cultivated at above 30° C.

5. The method of claim 1 wherein the microalgae are cultivated photoautotrophically outdoors in open ponds for at least 14 days under filtered sunlight.

6. The method of claim 1 further comprising bubbling $CO_2$ into the open ponds during cultivation.

7. The method of claim 1 wherein at least 20% of the fatty acids in the microalgae are eicosapentaenoic acid (EPA).

8. The method of claim 1 wherein the concentrated microalgae composition is a food grade dietary supplement.

9. The method of claim 1 wherein the concentrated microalgae composition is an aquaculture or animal feed.

10. A method of preparing a purified lipid composition comprising:
cultivating microalgae photoautotrophically outdoors in open ponds under filtered sunlight in continuous or batch mode at a dilution rate of less than 35% per day;
harvesting the microalgae in exponential phase when cell number is increasing at a rate of at least 20% of maximal rate of growth; and
concentrating the microalgae to obtain a concentrated microalgae composition having at least 40% of lipids in the microalgae in the form of glycodiacylglycerides, phosphodiacylglycerides, or a combination thereof and at least 5% by weight of fatty acids are docosahexaenoic acid (DHA), eicosapentaenoic acid (EPA), or a combination thereof; and
purifying lipids from the concentrated microalgae composition by extracting the lipids to obtain the purified lipid composition, wherein the purified lipids comprise at least 5% by weight EPA or DHA or a combination thereof;
wherein (a) the microalgae are *Tetraselmis* sp. and EPA yield in the microalgae is at least 10 mg/liter culture, (b) the microalgae are *Isochrvsis* sp. or *Pavlova* sp., (c) the microalgae are *Thalassiosira* sp. or *Chaetecoros* sp. and EPA yield in the microalgae is at least 10 mg/liter culture, or (d) the microalgae are *Tetraselmis* sp. and are cultivated at above 20° C. and EPA yield in the microalgae is at least 10 mg/liter culture.

11. The method of claim 10 wherein at least 20% of fatty acids in the purified lipids are EPA.

12. The method of claim 10 wherein at least 10% of fatty acids in the purified lipids are DHA.

13. The method of claim 10 wherein at least 40% of the EPA or DHA or both in the purified lipids are in glycodiacylglycerides or phosphodiacylglycerides or a combination thereof.

* * * * *